(12) United States Patent
Meijer et al.

(10) Patent No.: US 9,279,763 B2
(45) Date of Patent: Mar. 8, 2016

(54) APPARATUS AND METHOD FOR MEASURING AN ANALYTE SUCH AS BILIRUBIN, USING LIGHT

(75) Inventors: Eduard Johannes Meijer, Eindhoven (NL); Srinivas Rao Kudavelly, Karnataka (IN)

(73) Assignee: Koninklijke Philip N.V., Eindhoven (NL)

( * ) Notice: Subject to any disclaimer, the term of this patent is extended or adjusted under 35 U.S.C. 154(b) by 283 days.

(21) Appl. No.: 13/697,120

(22) PCT Filed: Apr. 27, 2011

(86) PCT No.: PCT/IB2011/051856
§ 371 (c)(1),
(2), (4) Date: Nov. 9, 2012

(87) PCT Pub. No.: WO2011/148280
PCT Pub. Date: Dec. 1, 2011

(65) Prior Publication Data
US 2013/0057865 A1    Mar. 7, 2013

Related U.S. Application Data

(60) Provisional application No. 61/348,880, filed on May 27, 2010.

(51) Int. Cl.
*G01N 21/25* (2006.01)
*G01N 21/49* (2006.01)
(Continued)

(52) U.S. Cl.
CPC .............. *G01N 21/49* (2013.01); *A61B 5/1455* (2013.01); *A61B 5/443* (2013.01); *G01N 21/255* (2013.01);
(Continued)

(58) Field of Classification Search
CPC ...... A61B 5/1455; A61B 5/1464; A61B 5/443
See application file for complete search history.

(56) References Cited

U.S. PATENT DOCUMENTS 4,985,737 A * 1/1991 Gaylord et al. ................. 257/15
5,353,790 A   10/1994 Jacques et al.
(Continued)

FOREIGN PATENT DOCUMENTS

| CN | 1051825 A | 5/1991 |
| RU | 2257144 | 7/2005 |
| WO | 9728437 | 8/1997 |

OTHER PUBLICATIONS

Gregory J. Newman; "Bilirubin Measurements in Neonates", Proceedings of the SPIE, vol. 3913, pp. 25-33, 2000.
(Continued)

*Primary Examiner* — Michael A Lyons
*Assistant Examiner* — Shawn Decenzo

(57) ABSTRACT

An analyte measuring device (5) for monitoring, for example, levels of a tissue analyte (e.g., bilirubin), includes a number of narrow band light sources (10), each narrow band light source being structured to emit a spectrum of light covering a number of wavelengths, and a number of detector assemblies (15) configured to receive light reflected from the transcutaneous tissues of a subject. Each of the detector assemblies includes a filter (20) and a photodetector (25), each filter being structured to transmit a main transmission band and one or more transmission sidebands, wherein for each narrow band light source the spectrum thereof includes one or more wavelengths that fall within the transmission band of at least one of the filters, and wherein for each narrow band light source the spectrum thereof does not include any wavelengths that fall within the one or more transmission sidebands of any of the optical filters.

18 Claims, 3 Drawing Sheets

(51) Int. Cl.
*A61B 5/1455* (2006.01)
*A61B 5/00* (2006.01)
*G01N 21/31* (2006.01)

(52) U.S. Cl.
CPC ... *G01N 2021/3144* (2013.01); *G01N 2021/3148* (2013.01); *G01N 2021/3177* (2013.01); *G01N 2021/3181* (2013.01); *G01N 2201/0627* (2013.01); *G01N 2201/0826* (2013.01)

(56) References Cited

U.S. PATENT DOCUMENTS

| | | | | |
|---|---|---|---|---|
| 5,477,326 | A | | 12/1995 | Dosmann |
| 6,040,578 | A | | 3/2000 | Malin et al. |
| 6,172,743 | B1 | | 1/2001 | Kley et al. |
| 6,230,046 | B1 | | 5/2001 | Crane et al. |
| 6,466,807 | B1 | * | 10/2002 | Dobson ............... A61B 5/14532 600/310 |
| 6,631,033 | B1 | * | 10/2003 | Lewis ........................... 359/584 |
| 6,847,835 | B1 | | 1/2005 | Yamanishi |
| 6,882,873 | B2 | * | 4/2005 | Samuels et al. ............... 600/315 |
| 6,927,843 | B2 | * | 8/2005 | Dick .................... A61B 5/0059 348/E5.096 |
| 7,812,712 | B2 | * | 10/2010 | White et al. ................ 340/426.2 |
| 2009/0137908 | A1 | * | 5/2009 | Patwardhan .................. 600/476 |

OTHER PUBLICATIONS

Steven L. Jacques et al; "Developing an Optical Fiber Reflectance Spectrometer to Monitor Bilirubinemia in Neonates", Proceeding of the SPIE, vol. 2975, pp. 115-124, Laser-Tissue Interactions, San Jose, CA, Feb. 1997.
"Practice Parameter: Management of Hyperbilirubinemia in the Healthy Term Newborn", American Academy of Pediatrics, vol. 94, No. 4, 1994, pp. 558-565.
Saidi et al, "Mie and Rayleigh Modeling of Visible-Light Scattering in Neonatal Skin", Applied Optics, vol. 34, No. 31, 1995, pp. 7410-7418.
Bland et al, Statistical Methods for Assessing Agreement Between Two Methods of Clinical Measurement, The Lancet, 1996, pp. 307-310.
Liu et al, "The Safety of Newborn Early Discharge: The Washington State Experience", JAMA, vol. 278, No. 4, 1997, pp. 293-298.
Maisels et al, "Length of Stay, Jaundice, and Hospital Readmission", Pediatrics, vol. 101, No. 6, 1998, pp. 995-998.
Hegyi, "Transcutaneous Bilirubinometry in the Newborn Infant: State of the Art", Journal of Clinical Monitoring, Vol. 2, No. 1, 1986, pp. 53-59.
Yamanouchi et al, "Transcutaneous Bilirubinometry: Preliminary Studies of Noninvasive Transcutaneous Bilirubin Meter in the Okayama National Hospital", Pediatrics, vol. 65, No. 2, 1980, pp. 195-202.
Gourley, "Bilirubin Metabolism and Kernicterus", Advances in Pediatrics, vol. 44, Chapter 6, 1997, pp. 173-229.

* cited by examiner

APPARATUS AND METHOD FOR MEASURING AN ANALYTE SUCH AS BILIRUBIN, USING LIGHT

FIELD OF THE INVENTION

The present invention relates to the an apparatus and method for measuring an analyte, such as a tissue analyte like bilirubin, using light, and, in one particular embodiment relates to estimation of tissue analyte levels in individuals, such as neonates, and more specifically, to an apparatus and method of determining transcutaneous bilirubin (TcB) and estimating total serum bilirubin (TSB) based thereon.

BACKGROUND

Neonatal jaundice is a yellowing of the skin and other tissues of a newborn infant. Typically, a bilirubin level of more than 5 mg/dL manifests clinical jaundice in neonates. Management of jaundiced neonates typically requires the measurement and monitoring of total serum bilirubin (TSB), which is most commonly determined by analyzing a plasma or serum sample from the infant. However, as will be appreciated, the drawing of blood from infants for such an analysis causes pain and trauma. This fact has lead to the development of a number of non-invasive techniques for estimation of TSB.

BRIEF SUMMARY OF THE INVENTION

One particular non-invasive method for estimation of TSB, known as Transcutaneous Bilirubinometry, involves measurement of transcutaneous bilirubin (TcB). The method relies on the high correlation between TcB and TSB. Transcutaneous Bilirubinometry devices work by directing light into the skin of the neonate and detecting specific wavelengths that are reflected back from the neonate's subcutaneous tissues. The number of wavelengths used varies among different devices. The detected optical signals are converted to electrical signals by a photodetector, such as a photodiode, and the electrical signals are analyzed by a controller to generate a TSB value based on the intensity of the reflected signals. In many such devices, a white light source is combined with a spectrometer to make the needed measurements. While effective, this solution is more expensive than it needs to be since not all spectral bands are used in the analysis to determine TSB. Similar problems exist for devices that use light to measure other tissue analytes, such as other blood or skin analytes. Similar problems also exist for devices that use light to measure other non-tissue analytes, such as devices that detect color in, for example, paint or colored surfaces.

Thus, there is room for improvement in the field of analyte analysis using light, such as Transcutaneous Bilirubinometry.

In one embodiment, an analyte measuring device for monitoring, for example and without limitation, tissue analyte levels (e.g., bilirubin levels), that includes a number of narrow band light sources, each narrow band light source being structured to emit a spectrum of light covering a number of wavelengths, and a number of detector assemblies configured to receive light reflected from a subject (e.g., the transcutaneous tissues of the subject). Each of the detector assemblies includes a filter and a photodetector, each filter being structured to transmit a main transmission band and one or more transmission sidebands, wherein for each narrow band light source the spectrum thereof includes one or more wavelengths that fall within the transmission band of at least one of the filters, and wherein for each narrow band light source the spectrum thereof does not include any wavelengths that fall within the one or more transmission sidebands of any of the optical filters.

In another embodiment, a method of estimating level of an analyte, such as a tissue analyte (e.g, bilirubin), of a subject, is provided that includes steps of directing light from a number of light sources toward the subject (e.g., toward the skin of the subject), each light source emitting a spectrum of light covering a number of wavelengths, wherein in response to the directing, reflected light is reflected by the subject (e.g., the transcutaneous tissues of the subject), filtering the reflected light using a number of filters, each filter being structured to transmit a main transmission band and one or more transmission sidebands, wherein for each light source the spectrum thereof includes one or more wavelengths that fall within the transmission band of at least one of the filters, and wherein for each light source the spectrum thereof does not include any wavelengths that fall within the one or more transmission sidebands of any of the filters, the filtering producing a filtered light associated with each filter, and determining an estimated analyte level, such as a bilirubin level, based on the filtered light associated with each filter.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
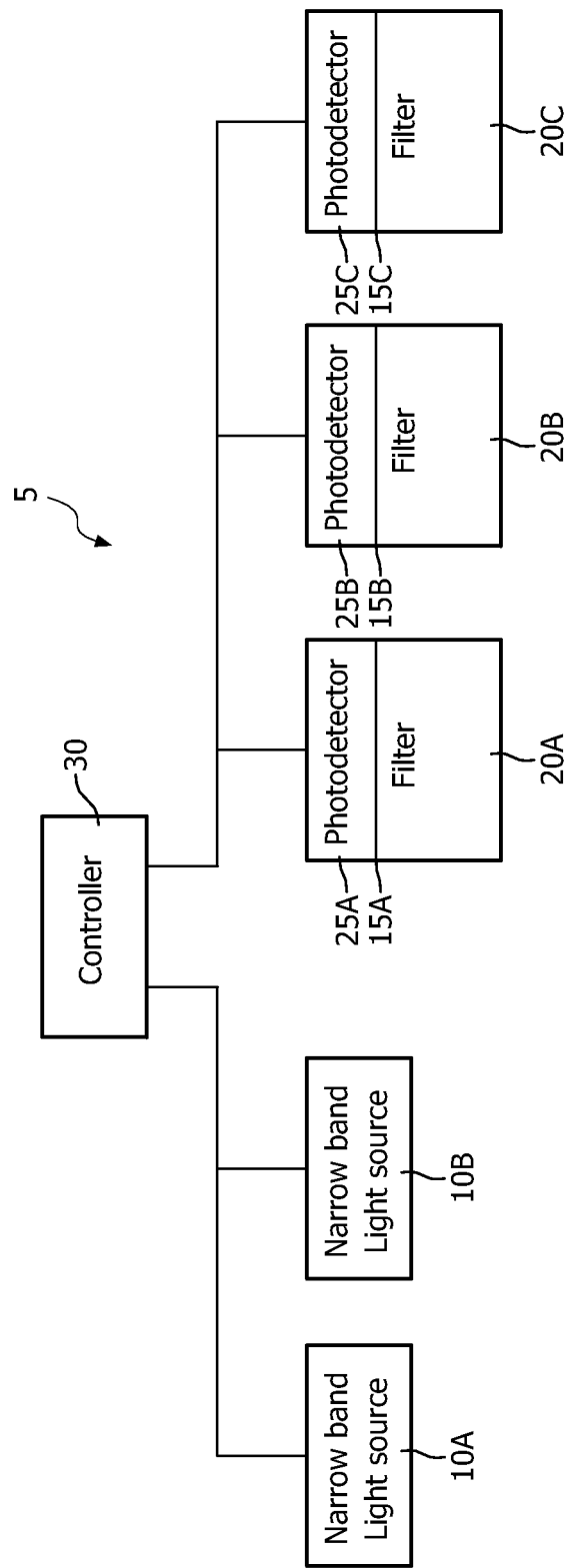
FIG. 1 is a block diagram of a bilirubin measuring device according to an exemplary embodiment of the present invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

The present invention relates the measurement of analytes, such as, without limitation, tissue analytes like bilirubin, using light analysis, and in particular to an apparatus and method for measuring such analytes. One such tissue analyte is bilirubin. For illustrative purposes, the present invention is described in connection with a device for monitoring bilirubin that is able to estimate bilirubin levels using Transcutaneous Bilirubinometry. It will be understood that that is meant to be exemplary, and that the present invention may be used to measure other tissue analytes, such as, without limitation, oxygen saturation ($SpO_2$), $VO_2$, melanin, and hemoglobin and hemoglobin components like methemoglobin, oxyhemoglobin, deoxyhemoglobin, carboxyhemoglobin, etc., or other non-tissues analytes such as color pigment.

FIG. 1 is a block diagram of bilirubin measuring device 5 according to an exemplary embodiment of the present invention. Bilirubin measuring device 5 includes a number of narrow band light sources 10, which in the illustrated embodiment are narrow band light source 10A and narrow band light source 10B (while two such narrow band light sources 10 are shown, that is meant to be exemplary only and it will be appreciated that more or less than two narrow band light sources 10 may also be used). Each narrow band light source 10A, 10B emits light in a separate transmission band region comprising a selected, limited range of wavelengths. Each narrow band light source 10A, 10B is thus not a white light source. Each narrow band light source 10A, 10B may be, for example and without limitation, an LED centered at a particular peak wavelength. Narrow band light sources 10A, 10B are structured and configured within bilirubin measuring device 5 to transmit light toward the skin of an individual, such as a neonate. For example, one or more optical fibers coupled to narrow band light sources 10A, 10B may be used to direct the light toward the skin of the subject.

Bilirubin measuring device 5 further includes a number of detector assemblies 15, which in the illustrated embodiment are detector assemblies 15A, 15B, 15C (while three such detector assemblies 15 are shown, that is meant to be exemplary only and it will be appreciated that more or less than thee detector assemblies 15 may also be used). Detector assemblies 15A, 15B, 15C are each structured to receive and detect light reflected from the subcutaneous tissue of an individual, such as a neonate. For example, one or more optical fibers may be coupled to each of the detector assemblies 15A, 15B, 15C to collect and direct the reflected light toward the detector assembly 15A, 15B, 15C. Each detector assembly 15A, 15B, 15C is, in the exemplary embodiment, shielded from all light except the light from the narrow band light sources 10A, 10B that is reflected.

Figure 2:
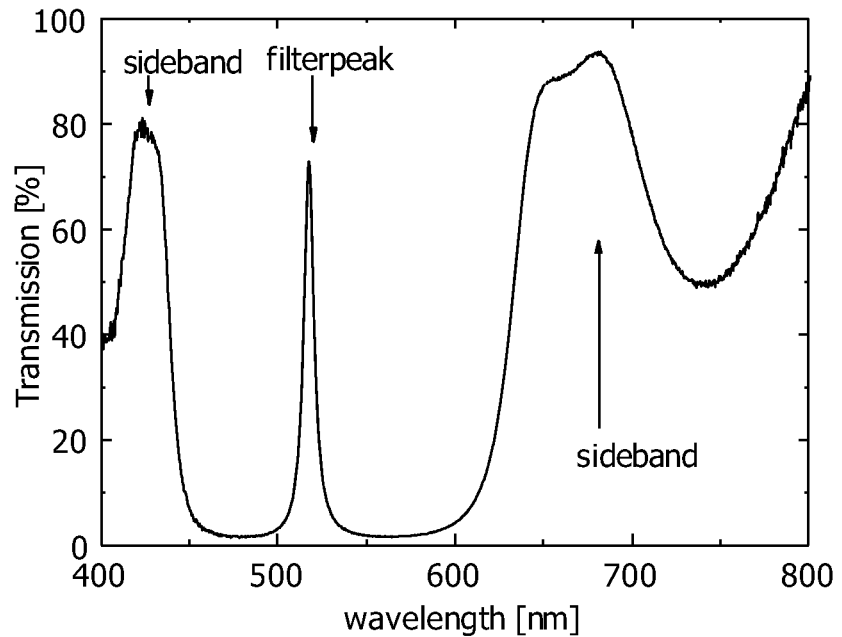
FIG. 2 is a graph of transmission versus wavelength for an exemplary optical filter that may be employed in the bilirubin measuring device of FIG. 1.

Each detector assembly 15A, 15B, 15C includes an optical filter 20A, 20B, 20C operatively coupled to (e.g., positioned on top of) an associated photodetector 25A, 25B, 25C. Each photodetector 25A, 25B, 25C is a device, such as, without limitation, a photodiode, that converts light into a current or voltage. Furthermore, each optical filter 20A, 20B, 20C is a band pass filter that is centered at a predetermined wavelength of light with a predetermined full-width at half maximum (FWHM). In addition, in the exemplary embodiment, each optical filter 20A, 20B, 20C is a filter that transmits a main transmission band and one or more transmission sidebands, such as, without limitation, an all-dielectric interference filter stack employing, for example, quarter wavelength mirrors. The transmission characteristics of such a filter are shown in FIG. 2, which illustrates a filter having a transmission band centered at 517 nm (with a FWHM of 5 nm) and at least two sidebands. All-dielectric interference filter stacks are advantageous because they have high transmission, good selectivity, and are relatively easy to fabricate on an industrial scale. In an exemplary embodiment, none of the transmission bands overlap one another.

According to an aspect of the invention, each narrow band light source 10A, 10B emits a spectrum of light that includes light of the center wavelength of one or more of the optical filters 20A, 20B, 20C. In addition, the emission spectrum of each narrow band light source 10A, 10B does not include any light that falls within the transmission sidebands of any of the optical filters 20A, 20B, 20C. By avoiding the emission of light within the transmission sidebands of each of the optical filters 20A, 20B, 20C, the spectral specificity of each optical filter 20 is able to be maintained.

Figure 3:
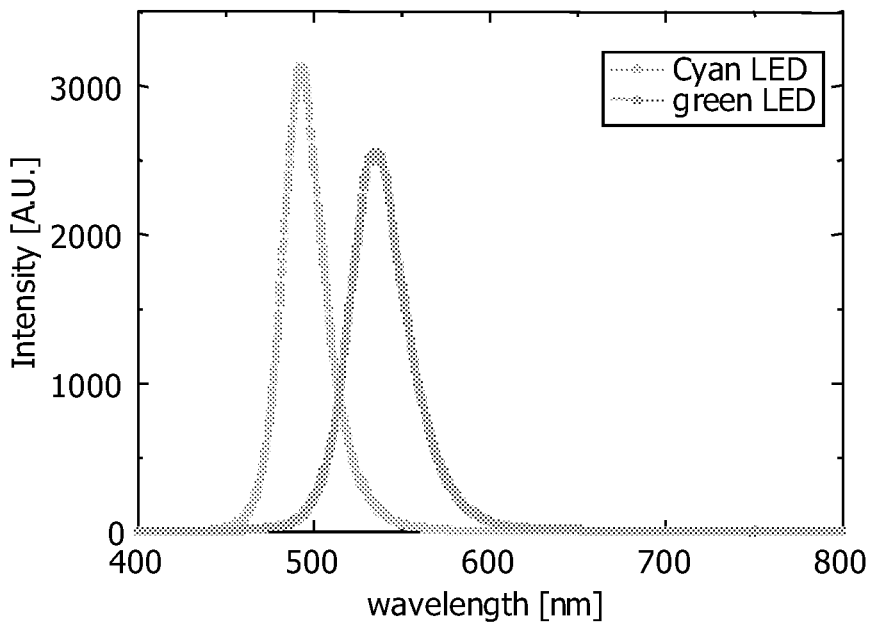
FIG. 3 is a graph of intensity versus wavelength for two narrow band light sources that may be used in a particular embodiment of the bilirubin measuring device of FIG. 1.
Figure 4:
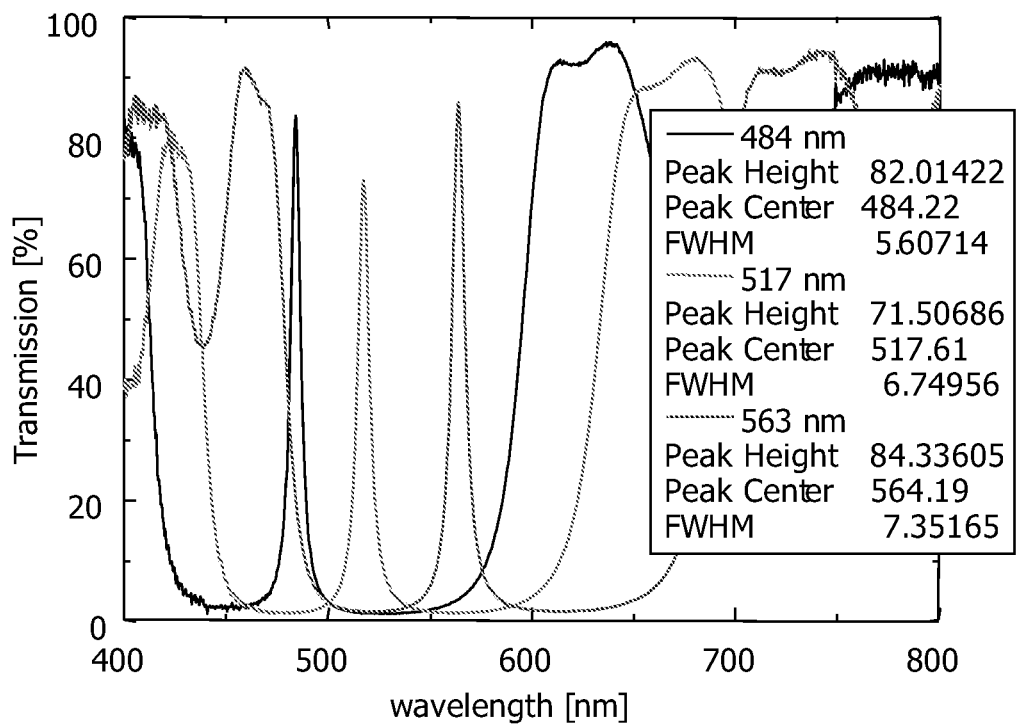
FIG. 4 is a graph of transmission versus wavelength for three optical filters that may be employed in a particular embodiment of the bilirubin measuring device of FIG. 1.
Figure 5:
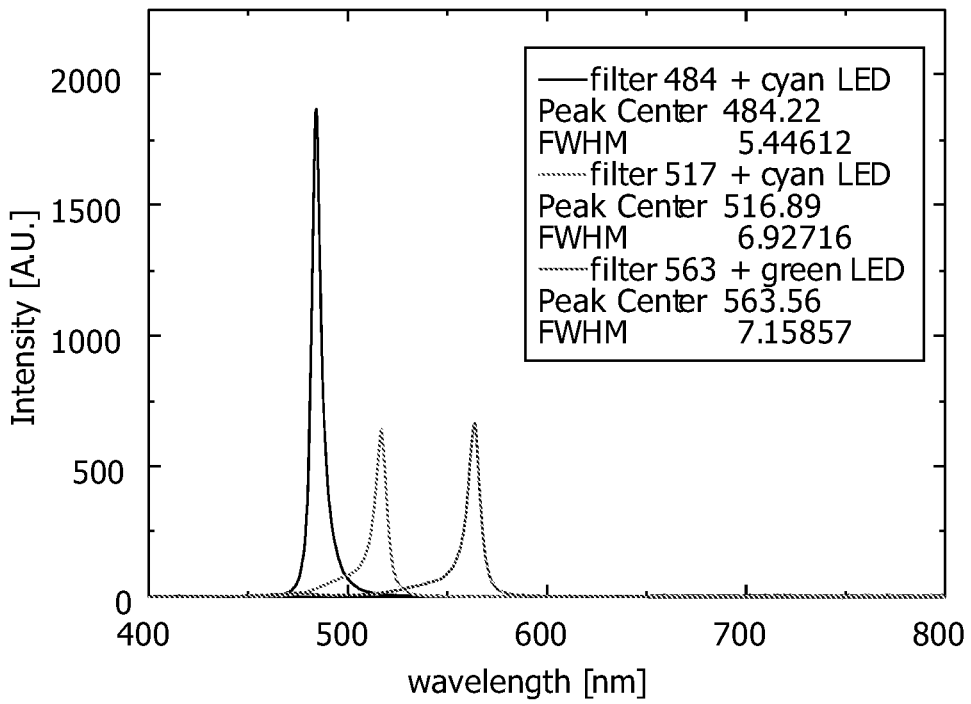
FIG. 5 shows the measured effective filter responses based on the filters of FIG. 4 illuminated by the light sources of FIG. 3.

In one particular, non-limiting embodiment, narrow band light source 10A is a cyan LED centered at about 485 nm and narrow band light source 10B is a green LED centered at about 530 nm. The emission characteristics of these light sources are shown in FIG. 3. In addition, in this embodiment, optical filter 20A is an all-dielectric interference filter stack that is centered at 484.22 nm with a FWHM of 5.60714 nm, optical filter 20B is an all-dielectric interference filter stack that is centered at 517.61 nm with a FWHM of 6.74956 nm, and optical filter 20C is an all-dielectric interference filter stack that is centered at 564.19 nm with a FWHM of 7.35165 nm. The transmission characteristics of each of these filters are shown in FIG. 4. FIG. 5 shows the measured effective filter responses based on the filters of FIG. 4 illuminated by the light sources of FIG. 3.

Furthermore, referring again to FIG. 1, bilirubin measuring device 5 also includes controller 30 that is operatively coupled to narrow band light sources 10A, 10B and detector assemblies 15A, 15B, 15C. Controller 30 includes a processing portion which may be, for example, a microprocessor, a microcontroller or some other suitable processing device, and a memory portion that may internal to the processing portion or operatively coupled to the processing portion and that provides a storage medium for data and software executable by the processing portion for controlling the operation of bilirubin measuring device 5, including calculating TcB and/or estimating TSB based on the intensity levels of the light detected by detector assemblies 15A, 15B, 15C. In operation, bilirubin measuring device 5 is placed against the skin of a subject, such as a neonate. Controller 30 then causes narrow band light sources 10A, 10B to emit and direct light toward the skin of the subject. Light that is reflected from the subcutaneous tissues is filtered by the optical filters 20A, 20B, 20C and detected by the photodetectors 25A, 25B, 25C, which each convert the detected light into an electrical signal (voltage or current). Those electrical signals are then provided to controller 30. Controller 30 will then calculate TcB and/or estimate TSB based on those signals using any of a number of known methodologies. Suitable methodologies are described in, for example, one or more of the following, the disclosures of which are incorporated herein by reference: U.S. Pat. Nos. 5,353,790; 6,847,835; 6,882,873; S. L. Jacques et al., "Developing an Optical Fiber reflectance Spectrometer to Monitor Bilirubinemia in Neonates", SPIE Proceedings 2975:115-124, *Laser-Tissue Interactions*, San Jose, Calif. February 1997; and G. J. Newman, "Bilirubin Measurements in Neonates," SPIE Vol. 3913 (2000), in *In Vitro Diagnostic Instrumentation*.

In one exemplary embodiment, bilirubin measuring device 5 is a fully integrated system, where both narrow band light sources 10A, 10B and detector assemblies 15A, 15B, 15C are positioned on the same measurement board, positioned slightly apart from the skin or measurement surface, to allow the light emitted by the narrow band light sources 10A, 10B to reflect back from that surface and back-reflect to the detector assemblies 15A, 15B, 15C. Care should be taken to prevent direct light from the narrow band light sources 10A, 10B from hitting the detector assemblies 15A, 15B, 15C. Rather, only reflected light should be permitted to do so.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An analyte measuring device, comprising multiple narrow band light sources and multiple detector assemblies, wherein
the multiple detector assemblies include:
a first detector assembly configured to receive light emitted by the multiple narrow band light sources and reflected by a subject, the first detector assembly including a first filter coupled to a first photodetector, wherein the first filter is configured such that light having wavelengths in a main transmission band of the first filter passes through and such that light having wavelengths in one or more transmission sidebands of the first filter passes through;
a second detector assembly configured to receive light emitted by the multiple narrow band light sources and reflected by the subject, the second detector assembly including a second filter coupled to a second photodetector, wherein the second filter is configured such that light having wavelengths in a main transmission band of the second filter passes through and such that light having wavelengths in one or more transmission sidebands of the second filter passes through; and
a third detector assembly configured to receive light emitted by the multiple narrow band light sources and reflected by the subject, the third detector assembly including a third filter coupled to a third photodetector, wherein the third filter is configured such that light having wavelengths in a main transmission band of the third filter passes through and such that light having wavelengths in one or more transmission sidebands of the third filter passes through; and
the multiple narrow band light sources include:
a first narrow band light source being structured to emit a first narrow band spectrum of light covering a first set of wavelengths, wherein the first set of wavelengths includes wavelengths that fall within the main transmission band of one or more of the first filter, the second filter, and the third filter, and wherein the first set of wavelengths does not include any wavelengths that fall within the transmission sidebands of the first filter, the second filter, or the third filter; and
a second narrow band light source being structured to emit a second narrow band spectrum of light covering a second set of wavelengths, wherein the second set of wavelengths includes wavelengths that fall within the main transmission band of one or more of the first filter, the second filter, and the third filter and wherein the second set of wavelengths does not include any wavelengths that fall within the transmission sidebands of the first filter, the second filter, or the third filter;
wherein one or both of the first narrow band light source and the second narrow band light source being structured to emit a narrow band spectrum of light covering wavelengths that fall within the main transmission bands of at least two of the filters.

2. The measuring device according to claim 1, wherein the subject is a human and wherein the analyte is a tissue analyte.

3. The measuring device according to claim 2, wherein the tissue analyte is bilirubin, wherein the multiple detector assemblies are configured to receive light emitted by the multiple narrow band light sources and reflected by transcutaneous tissues of the subject, and wherein the main transmission bands of the filters of the multiple detector assemblies include multiple predetermined wavelengths suitable for determining one or both of a transcutaneous bilirubin (TCB) level and a total serum bilirubin (TSB) level of the subject.

4. The measuring device according to claim 3, further comprising a controller (30) operatively coupled to the multiple narrow band light sources and the multiple detector assemblies, wherein individual photodetectors included in the multiple detector assemblies are configured to generate individual electrical signals based on light received by the individual photodetectors, and wherein the controller is adapted to determine one or both of the TCB level and the TSB level of the subject based on the individual electrical signals received from the individual photodetectors.

5. The measuring device according to claim 3, wherein individual ones of the multiple detector assemblies are shielded from all light except the light reflected by the transcutaneous tissues of the subject.

6. The measuring device according to claim 1, wherein individual ones of the filters are centered at a predetermined wavelength of light and have a predetermined full-width at half maximum.

7. The measuring device according to claim 6, wherein the first narrow band light source includes a cyan LED and wherein the second narrow band light source includes a green LED, and wherein the filters of the multiple detector assemblies include a first filter centered at 484.22 nm with a full-width at half maximum (FWHM) of 5.60714 nm, a second filter centered at 517.61 nm with a FWHM of 6.74956 nm, and a third filter centered at 564.19 nm with a FWHM of 7.35165 nm.

8. The measuring device according to claim 6, wherein individual ones of the filters are an all-dielectric interference filter stack.

9. The measuring device according to claim 1, wherein at least one photodetector is a photodiode.

10. A method of measuring an analyte of a subject, comprising:
directing light from multiple narrow band light sources including a first narrow band light source and a second narrow band light source toward the subject, wherein individual ones of the multiple narrow band light sources emit a narrow-band spectrum of light covering a number of wavelengths, wherein responsive to the directing, emitted light is reflected by the subject;
filtering the reflected light using multiple filters, the filters including a first filter coupled to a first photodetector, a second filter coupled to a second photodetector, and a third filter coupled to a third photodetector, wherein individual ones of the multiple filters have a main transmission band and one or more transmission sidebands, wherein:

for individual ones of the multiple narrow band light sources the emitted narrow-band spectrum includes one or more wavelengths that fall within the main transmission band of at least one of the multiple filters, wherein one or both of the first narrow band light source and the second narrow band light source being structured to emit a narrow band spectrum of light covering wavelengths that fall within the main transmission bands of at least two of the filters, and for individual ones of the multiple narrow band light sources the emitted narrow-band spectrum does not include any wavelengths that fall within the one or more transmission sidebands of any of the multiple filters, the filtering producing a filtered light associated with individual ones of the multiple filters; and determining a measurement relating to the analyte based on the filtered light associated with individual ones of the multiple filters.

11. The method according to claim 10, wherein the analyte is a tissue analyte of the subject, wherein the directing comprises directing light from the multiple narrow band light sources toward the skin of the subject, and wherein in response to the directing, the reflected light is reflected by transcutaneous tissues of the subject.

12. The method according to claim 11, wherein the tissue analyte is bilirubin and the method is a method of estimating a bilirubin level of the subject, wherein the determining a measurement relating to the analyte includes determining an estimated bilirubin level based on the filtered light associated with individual ones of the multiple filters.

13. The method according to claim 12, wherein the main transmission bands of the multiple filters include a plurality of predetermined wavelengths required for determining one or both of a transcutaneous bilirubin (TCB) level and a total serum bilirubin (TSB) level of the subject.

14. The method according to claim 12, further comprising generating individual electrical signals based on the filtered light, wherein determining the estimated bilirubin level includes determining one or both of the TCB level and the TSB level of the subject based on the individual electrical signals associated with the filtered light produced by individual ones of the multiple filters.

15. The method according to claim 10, wherein individual ones of the multiple filters are centered at a predetermined wavelength of light and have a predetermined full-width at half maximum.

16. The method according to claim 15, wherein the first narrow band light source emits cyan light and wherein the second light source emits green light, and wherein the multiple filters include a first filter centered at 484.22 nm with a full-width at half maximum (FWHM) of 5.60714 nm, a second filter centered at 517.61 nm with a FWHM of 6.74956 nm, and a third filter centered at 564.19 nm with a FWHM of 7.35165 nm.

17. The method according to claim 15, wherein individual ones of the multiple filters are an all-dielectric interference filter stack.

18. The method according to claim 10, further comprising shielding the multiple filters from all light except the reflected light.

* * * * *